(12) United States Patent
Lombardo et al.

(10) Patent No.: US 9,173,652 B2
(45) Date of Patent: Nov. 3, 2015

(54) ALL-SUTURE ANCHOR INSERTER

(71) Applicants: Giuseppe Lombardo, New Port Richey, FL (US); Peter C. Miller, Largo, FL (US); Steven E. Fitts, Largo, FL (US)

(72) Inventors: Giuseppe Lombardo, New Port Richey, FL (US); Peter C. Miller, Largo, FL (US); Steven E. Fitts, Largo, FL (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 13/815,577

(22) Filed: Mar. 11, 2013

(65) Prior Publication Data

US 2014/0257383 A1 Sep. 11, 2014

(51) Int. Cl.
*A61B 17/04* (2006.01)

(52) U.S. Cl.
CPC ...... *A61B 17/0401* (2013.01); *A61B 2017/0404* (2013.01); *A61B 2017/0406* (2013.01); *A61B 2017/0409* (2013.01); *A61B 2017/0464* (2013.01)

(58) Field of Classification Search
CPC ............... A61B 2017/0411; A61B 2017/0488; A61B 2017/0409; A61B 17/0466; A61B 17/16; A61B 17/1604; A61B 17/1635; A61F 2002/0888
USPC .................. 606/232, 129, 132, 138, 139, 104, 606/309–312, 83–85; 623/13.14; 411/76, 411/512; 30/322, 353
See application file for complete search history.

(56) References Cited

U.S. PATENT DOCUMENTS

| | | | | |
|---|---|---|---|---|
| 5,372,599 | A * | 12/1994 | Martins | 606/75 |
| 6,156,039 | A * | 12/2000 | Thal | 606/232 |
| 6,290,702 | B1 * | 9/2001 | Fucci et al. | 606/323 |
| 6,524,316 | B1 * | 2/2003 | Nicholson et al. | 606/326 |
| 7,381,213 | B2 * | 6/2008 | Lizardi | 606/232 |
| 7,749,250 | B2 * | 7/2010 | Stone et al. | 606/232 |
| 2012/0245631 | A1 * | 9/2012 | Lunn et al. | 606/232 |
| 2013/0060288 | A1 * | 3/2013 | Rodgers et al. | 606/281 |
| 2013/0103081 | A1 * | 4/2013 | Wolf | 606/232 |
| 2013/0144334 | A1 * | 6/2013 | Bouduban et al. | 606/232 |
| 2014/0114330 | A1 * | 4/2014 | Karasic et al. | 606/144 |

* cited by examiner

*Primary Examiner* — Todd Manahan
*Assistant Examiner* — Erich Herbermann
(74) *Attorney, Agent, or Firm* — David L. Nocilly; Bond Schoeneck & King, PLLC (57) ABSTRACT

An inserter for simultaneously creating a bone tunnel and delivering an all-suture anchor. The inserter is capable of inserting into the bone tunnel a soft, non-rigid suture anchor by forming a bone tunnel (to serve as an anchor receiving area) and simultaneously, in one motion, delivering the soft suture anchor to the anchor receiving area. The soft suture anchor is made entirely of non-rigid materials including, but not limited to, filaments of soft, malleable materials such as those commonly used to make sutures. The inserter is able to not only carry or deliver the all-suture anchor into a bony substrate, but is able to do so without having to preform a hole in the bone.

8 Claims, 6 Drawing Sheets

ALL-SUTURE ANCHOR INSERTER

BACKGROUND OF THE INVENTION

1. Field of the Invention

This invention relates to all-suture anchors made entirely of suture material and inserters for inserting such anchors into tissue at a surgical site. More particularly, this invention relates to devices for percutaneously inserting or driving all-suture anchors into a surgical site.

2. Description of the Prior Art

Anchors are commonly employed during surgical procedures to provide a reliable attachment location for sutures in or against a substrate, those attached sutures then being used to capture and retain other objects, such as soft tissue or bone. The substrate may be bony tissue or soft tissue such as ligaments, tendons, etc. In the case of bony tissue, suture anchors are generally inserted into and retained in a pre-formed hole in the bone, so that suture extends from the anchor out of the hole. In the case of soft tissue, suture anchors generally are placed on a side of the soft tissue such that suture extends through a hole in the tissue to extend beyond the soft tissue on a side opposite the anchor.

Soft suture anchors have recently been developed from filaments of suture material which are retained within pre-formed bone holes by being deformable to increase their diameter to a size greater than that of the bone hole, to thereby reside within the cancellous bone and under the bone cortex. One such suture anchor is disclosed in U.S. Patent Publication 2012/0290004, published Nov. 15, 2012, assigned to the assignee hereof and incorporated by reference herein. Since soft anchors are commonly made entirely of suture materials, they are sometimes called "all-suture" anchors.

The necessity for a pre-formed hole when using all-suture anchors in bone requires extra instrumentation and extra steps in the process of implanting soft suture anchors. The extra steps involve making a pilot hole in the bone with either a drill, a broach or a punch and then removing the instrument. The hole thus created is an anchor receiving area, but once this space is created the instrument must be removed to allow the all-suture anchor to be inserted by an inserter and then deployed. While so-called "self-punching" inserters, drivers or applicators have been known to be used with some suture anchors which are hard enough to withstand the stresses of insertion without pre-drilling, there remains a need for a self-punching inserter for soft, all-suture anchors.

Accordingly, it is an object of this invention to produce a self-punching inserter suitable for inserting all-suture anchors into bone.

It is another object of this invention to produce a self-punching inserter capable of percutaneously driving an all-suture anchor into place at a surgical site.

SUMMARY OF THE INVENTION

These and other objects of the present invention are achieved by a soft anchor inserter system as described herein which enables the creation of the anchor receiving area in a bony substrate and the delivery of an all-suture anchor into that space, both in a single step.

In one aspect, the invention is an all-suture anchor inserter for inserting an all-suture anchor into a bone substrate without first, separately, forming a hole to receive the anchor. The inserter comprises a passage forming portion for being pushed into the substrate to therein create an anchor receiving area and an all-suture anchor carrying portion immediately adjacent the passage forming portion for delivering said all-suture anchor into the anchor receiving area.

In another aspect, the invention is an all-suture anchor inserter comprising an elongated shaft having an axis, a proximal end and a distal end, the distal end comprising a pair of longitudinally aligned and distally extending tines situated on opposite sides of the axis. Each of the tines comprises a distally facing planar tip surface and a tapered, radially outward, distally and laterally facing surface proximal to the planar tip surface. Each tine further comprises a flat radially inward lateral surface situated in a plane parallel to the axis and opposite the tapered, radially outward, distally and laterally facing surface. Each tine also comprises a pair of opposed, tapered, distally and laterally facing surfaces perpendicular to the radially inward lateral surface and extending between the inward lateral surface and the tapered, radially outward distally and laterally facing surface for a predetermined longitudinal distance along the length of the tines. In a preferred embodiment the tapered, radially outward, distally and laterally facing surfaces proximal to the planar tip surfaces are conically shaped and may further be convex so as to enhance the laterally directed forces pushing the bone away from the axis of the inserter.

A preferred embodiment of the invention further comprises an inserter wherein the passage forming portion comprises a diametrically opposed pair of tines provided with tapered bone cutting surfaces and wherein the anchor carrying portion comprises a longitudinally extending space between the tines.

DESCRIPTION OF THE PREFERRED EMBODIMENT

This invention pertains to the percutaneous insertion of a soft, non-rigid suture anchor construct preloaded onto an inserter (also sometimes called a driver or applicator) which is "self-punching". The preferred embodiment of the soft suture anchor disclosed herein is a suture anchor which is entirely comprised of soft, compressible and distendable materials. Commonly used for such purposes are filaments of suture materials (hence, the term "all-suture") made of, for example, polyester or, preferably, Ultra High Molecular Weight Polyethylene (UHMWPE).

Figure 1:
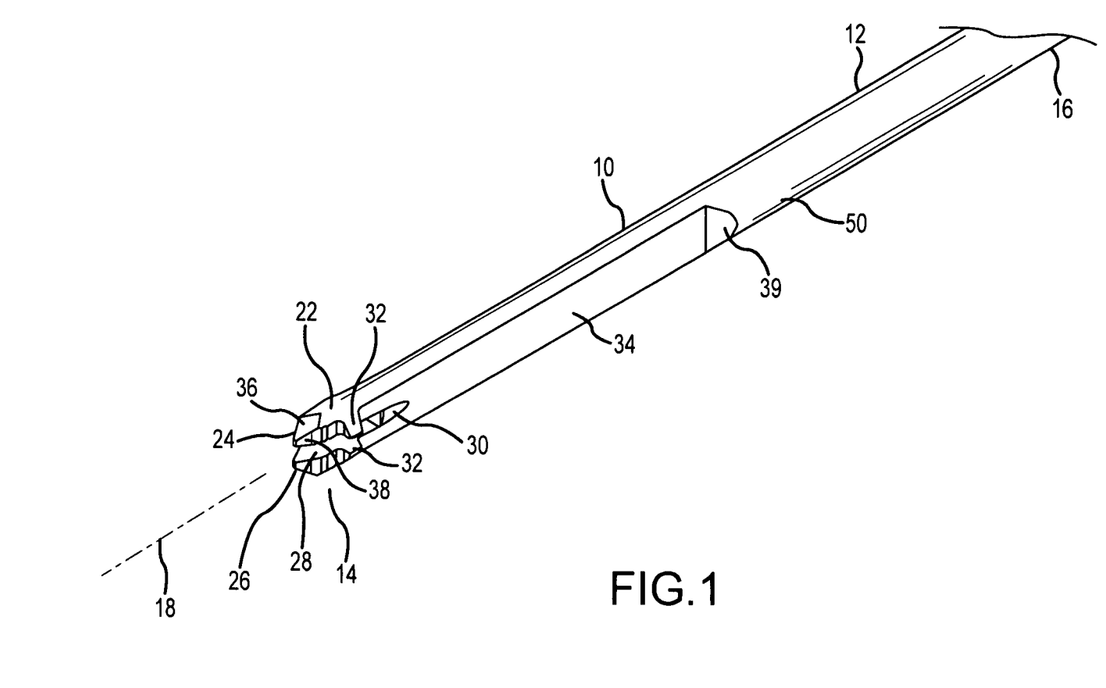
FIG. 1 is a perspective view of the distal end of an all-suture anchor inserter constructed in accordance with the principles of this invention.
Figure 2:
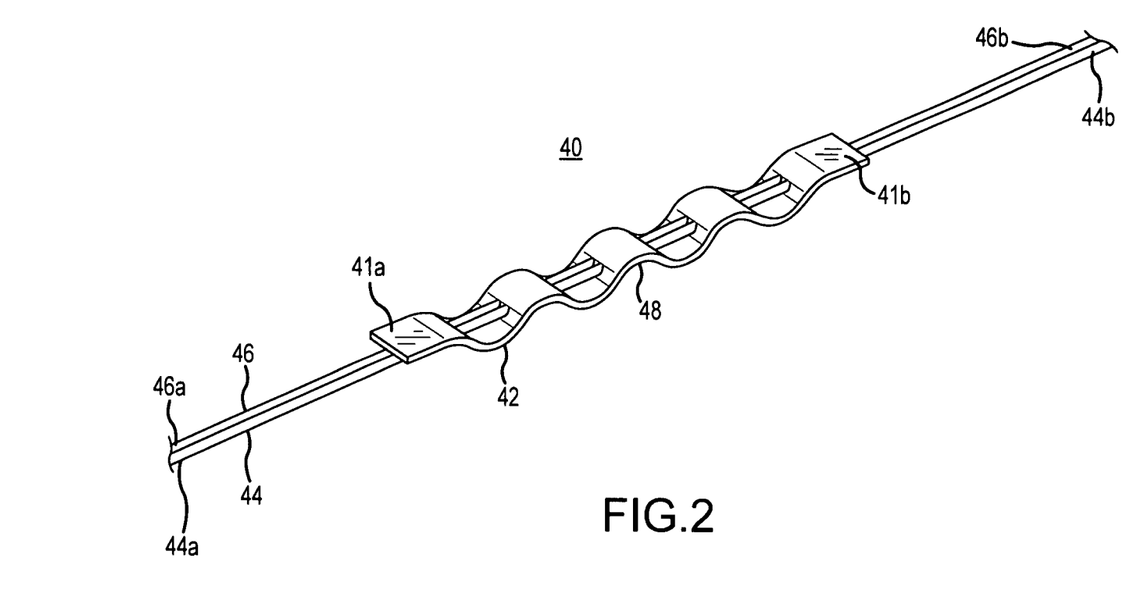
FIG. 2 is a perspective view of an all-suture anchor as seen during a portion of its manufacture.

An example of a prior art all-suture anchor designed to be inserted into place at a surgical work site is shown in FIG. 2, and a preferred embodiment of an inserter which is intended to insert this anchor, and which is the subject matter of this invention, is shown in FIG. 1. The distinction between the subject invention and that disclosed in the aforementioned prior publication is that the inserter disclosed herein is further adapted to enable percutaneous insertion through the skin and soft tissue directly into the bone at the surgical site without predrilling or otherwise forming a hole in the bone.

A preferred embodiment of the invention disclosed herein comprises an all-suture anchor inserter which has a passage forming, distally facing distal tip portion followed, upon insertion and without having to remove the passage forming portion, by an anchor carrying portion which supports and delivers (e.g. by pushing) the all-suture anchor into the passageway formed by the distal tip portion.

The body (referred to below as web 42) of the all-suture anchor, even after it is interwoven with a suture filament to become a filament-carrying body, is malleable and non-rigid so it cannot be pushed into a bone tunnel in the same manner that a conventional rigid suture anchor can be. The term "pushing" is commonly used with rigid suture anchors because it reflects the fact that the prior art, rigid anchor inserters "push" the rigid suture anchors into place by applying a distally directed force to the proximal-most, proximally facing surface of the rigid anchors. However, an all-suture anchor having a malleable body with little or no column strength cannot really be "pushed". Therefore, use of the term "push" is slightly misleading. While the term "push" has come to be commonly used with respect to the insertion of all-suture anchors into a bone hole, it is more technically accurate to say the all-suture anchor is "pulled" into place. That is, "pushing" on the distal-most part of the all-suture anchor has the effect of actually pulling the anchor into position. The distal-most parts of the anchor enter the bone tunnel first, with the trailing (i.e., proximal) parts of the anchor being pulled along by the distal parts, and this is true whether the body of the all-suture anchor is folded back on itself, to enable it to be pushed at a midpoint, or straight, to enable it to be pushed at the distal end. Nevertheless, the term "push" may still be used herein when applied to all-suture anchors.

FIG. 2 shows an all-suture anchor 40 which comprises, for example, a fibrous, braided or woven fabric-type structure such as flexible web 42 of ribbon-like or tape-like material which is assembled by interweaving filaments 44 and 46 through web 42 as shown to form a construct which, when folded on itself about center point 48 (as best seen in FIGS. 5-8), becomes an undeployed all-suture anchor 40 carried by inserter 10. The deployment of this type of construct and its deformation within a bone tunnel are more fully explained in the aforementioned U.S. patent publication. It will be understood that in the preferred embodiment web 42 is, in an undeployed state, formed as a substantially flat tape-like element having a rectangular cross-section when viewed end-on. However, it can also have a variety of other cross sectional configurations such as circular, oval, etc. (While FIG. 2 shows web 42 as having an undulating structure, this is exaggerated merely to convey the soft nature of the web material. (Compare this to FIGS. 5-8 where web 42 is shown in a flat folded configuration.)

As shown in FIG. 2, all-suture anchor 40 comprises a plurality of parallel filaments of suture material woven through a ribbon-shaped element which can itself be made of filaments of suture material. For example, in a preferred embodiment web 42 may be a piece of conventional suture tape. It will be understood, however, that the ribbon-shaped element 42 need not literally be formed of suture filaments and other methods may be used to manufacture this element provided that it performs the same or substantially the same as the preferred embodiment disclosed herein. One can envision, for example, other soft constructs such as molded, woven or braided structures made of soft, deformable material not normally used for sutures (although they would need to be biocompatible of course). The construct may be formed of parallel filaments or randomly interlaced or entangled filaments, short pieces of fiber, etc. In view of the above, the term "all-suture" as used herein includes all structures such as all-suture anchor 40 constructed of suitable soft materials, whether or not such materials are actually suture materials.

Figure 3:
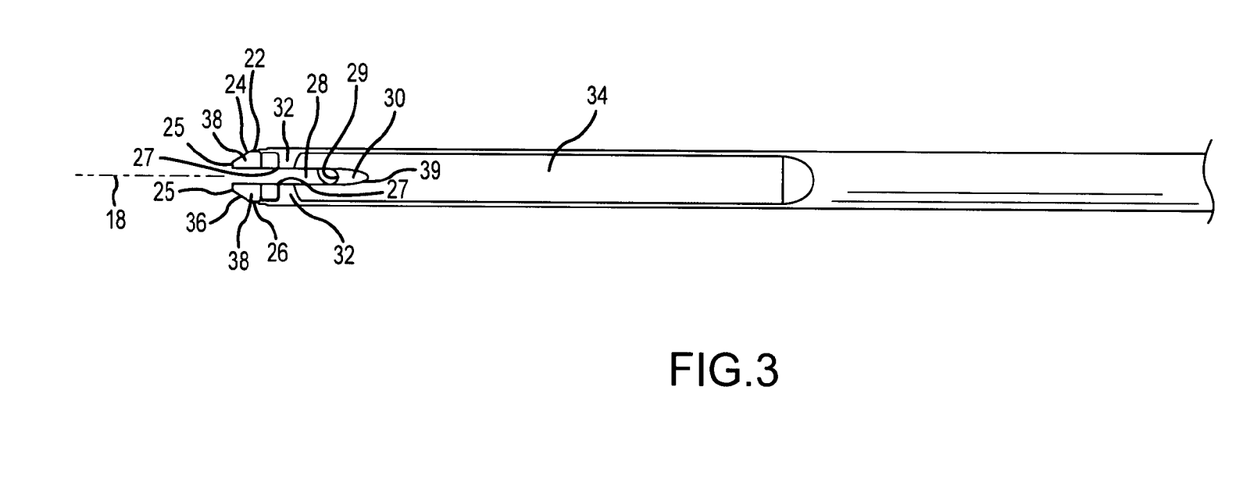
FIG. 3 is a side elevational view of FIG. 1.
Figure 4:
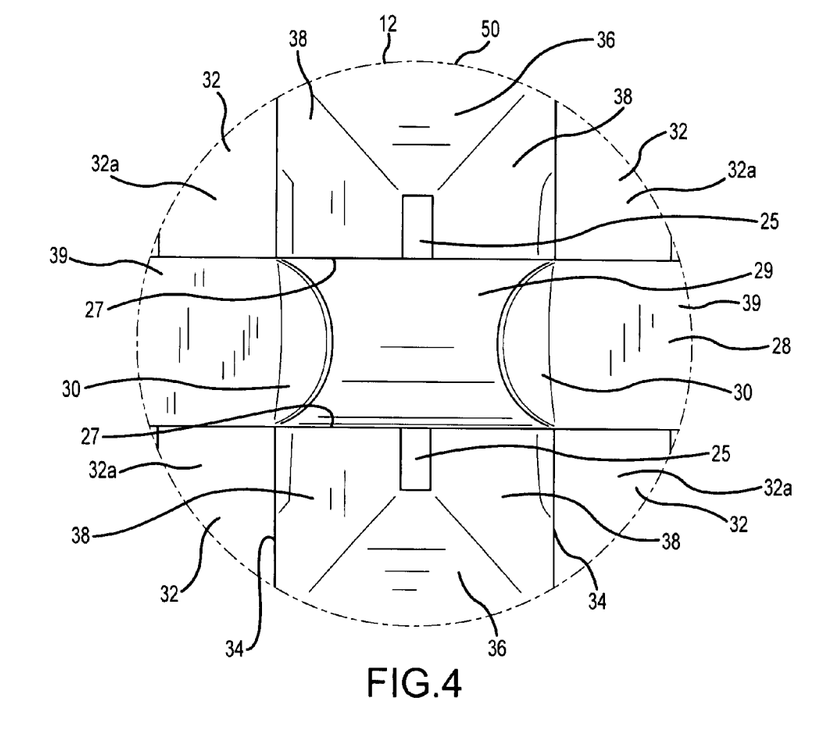
FIG. 4 is an end-on elevation view of the distal end of the inserter of FIG. 1.
Figure 5:
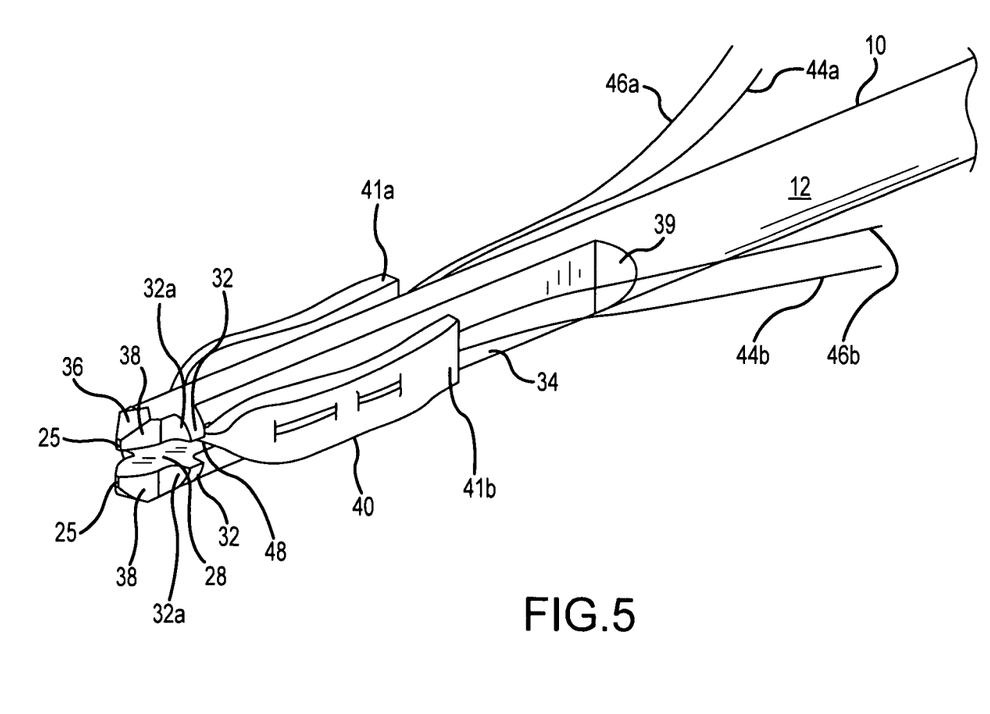
FIG. 5 is a perspective view of the inserter of FIG. 1 with the all-suture anchor of FIG. 2 assembled on the inserter and shown in an undeployed state.
Figure 6:
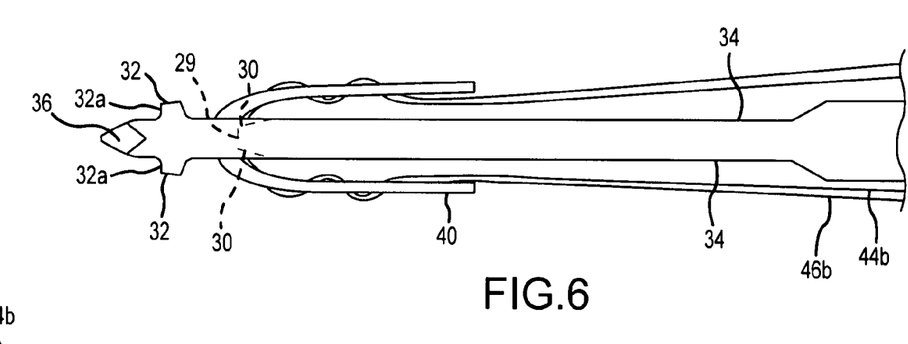
FIG. 6 is a top plan view of FIG. 5.
Figure 7:
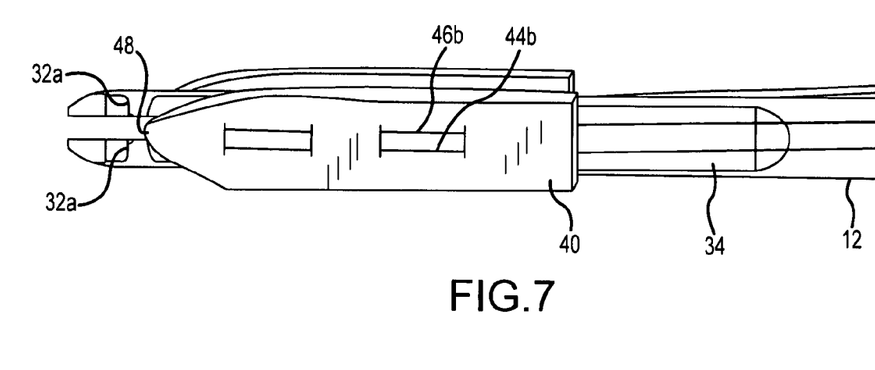
FIG. 7 is a side elevation view of FIG. 5.
Figure 8:
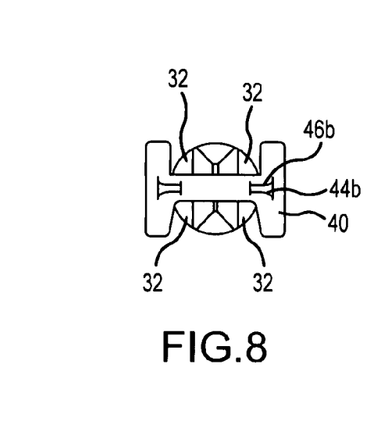
FIG. 8 is an end-on elevation view of the distal end of the inserter of FIG. 7.

As shown in FIG. 1, inserter or driver 10 is a preferred embodiment of the invention and comprises an elongated shaft 12 having a distal end 14, a proximal end 16 and an axis 18. Proximal end 16 can be attached to a handle (not shown) to facilitate use of the inserter. Distal end 14 is provided with a forked structure 22 having a pair of tines 24, 26 symmetrically situated on opposite sides of axis 18 with a longitudinally extending slot 28 therebetween. The flat, radially inward, lateral surfaces 27 of tines 24 and 26 are situated in a plane parallel to axis 18 and form the lateral boundary of slot 28. Slot 28 is adapted to receive the all-suture anchor 40 folded about surface 29 at the proximal-most end of slot 28 as best seen in FIGS. 3, 4 and 5. (In an alternative embodiment shaft 12 may, depending on the application, be cannulated with an axial lumen adapted to receive a guide wire which could be pierced through the fold at point 48 of the construct 40.)

Unlike the inserter shown in the aforementioned patent publication, in order to minimize the resistance encountered by the distally facing area of distal end 14 as the tip of inserter 10 pierces the cortical bone and broaches a hole in the bone, various tapering and relief surfaces and edges are formed at distal end 14. For example, as best seen in FIGS. 1 and 4, each tine 24 and 26 of the inserter distal end 14 contains a tapered, optionally slightly convex, radially outward, distally and laterally facing surface 36 formed at its distal end. These surfaces are immediately proximal to distally facing planar tip surfaces 25. Surfaces 36 are designed to deflect the tines radially inwardly to counteract forces which may otherwise cause the tines 24, 26 to splay open as end 14 is pushed into the bone. Surfaces 25 are perpendicular to axis 18 and are designed to concentrate distally directed forces from the inserter to the cortical bone. Relief is also provided by two diametrically opposed tapering cuts 30 at the base of slot 28. These cuts serve to taper the overall transverse size of the anchor/inserter assembly to facilitate the insertion of the assembly into the bone hole. The distal ends of taper cuts 30 blend smoothly into convex surface 29 formed at the proximal-most end of slot 28.

A preferred embodiment of the invention includes, at the approximate longitudinal midpoint of slot 28, four opposed broaching projections 32 having distally facing surfaces 32a which serve as a broaching feature to facilitate cutting through bone to reduce the frictional resistance encountered by anchor 40 as it passes through the cortical bone. These projections extend laterally in substantially opposite directions from each of the tines. Behind (i.e., distally of) the slot 28 are two opposed flat surfaces 34 designed to provide clearance for web ends 41a and b, and sutures 44a, b and 46a, b to pass alongside inserter 10 to minimize interference with the cortical bone. The proximal-most ends 39 of surfaces 34 are tapered to blend in with the cylindrical surface 50 of shaft 12. Also, opposite lateral sides of tine 24 are provided with distally and laterally facing broaching surfaces 38 which are perpendicular to the lateral surface 27 on one side of the tine. Symmetrical surfaces 38 are also formed on opposed sides of tine 26. Surfaces 38 also facilitate cutting/broaching the bone as inserter 10 is advanced and, in the preferred embodiment, are slightly convex. It will also be understood that the preferred embodiment includes rounded edges and corners between adjacent surfaces (e.g., 38 and 32a) as needed to facilitate manufacture and performance.

All-suture anchor 40 can be externally loaded onto inserter 10. As used herein, "externally loaded" means, as best seen in FIG. 5, that the construct 40 is attached to the inserter with the construct (which includes the sutures) lying along the surface of the inserter. In a preferred embodiment construct 40 is folded on itself about the distal end of inserter 10 such that suture ends 44a and b and 46a and b extend proximally relative to inserter distal end 14 along the outer surface of shaft 12. Alternatively, the construct could be "internally" loaded if the construct 40 and inserter 10 were to be inserted into a tubular sheath (not shown) to thereby protect the construct until it could be pushed distally from the sheath. One concern with this alternative is that it makes the assembled structure larger in diameter and, therefore, possibly unsuitable for certain applications.

It will be understood that a different embodiment of the invention could be constructed with a soft construct having a linear structure which is attached to the inserter by means other than being folded upon itself. For example, a linear ribbon-like construct could have one or more filaments threaded therethrough with the distal end of the filament(s) knotted or otherwise engaged on one side of tines 24, 26 and the ribbon body extending proximally from the tip on the other side of tines.

The preferred embodiment of inserter 10 is comprised of stainless steel or other biocompatible material hard enough to form a hole in the bone without drilling. The sizes of the construct 40 and inserter 10 may vary depending on the forces encountered in various applications, bone density, etc.

It will be understood by those skilled in the art that numerous improvements and modifications may be made to the preferred embodiment of the invention disclosed herein without departing from the spirit and scope thereof.

What is claimed is:

1. An all-suture anchor inserter, comprising:
    an elongated shaft;
    a pair of tines positioned at one end of the shaft to define a passage forming portion for being pushed into a bone to therein create an anchor receiving area, wherein the tines are spaced apart to define a slot therebetween that forms an all-suture anchor carrying portion that is immediately proximal to said passage forming portion such that an all-suture anchor positioned in said all-suture carrying portion with be advanced into said anchor receiving area of said bone after said passage forming portion has formed said anchor receiving area; and
    a pair of broaching projections extending outwardly and oppositely from each of said pair of tines.

2. An inserter according to claim 1 wherein said pair of tines include tapered, distally and laterally facing bone cutting surfaces.

3. An all-suture anchor inserter according to claim 2, wherein said passage forming portion further comprises a plurality of circumferentially arranged, distally facing bone cutting surfaces.

4. An all-suture anchor inserter for inserting an all-suture anchor into a bone comprising:
    an elongated shaft having an axis, a proximal end and a distal end, said distal end comprising a pair of longitudinally aligned and symmetrical, distally extending tines situated on opposite sides of said axis, each of said tines comprising a distally facing planar tip surface, a tapered, radially outward, distally and laterally facing surface proximal to said planar tip surface, a flat radially inward lateral surface situated in a plane parallel to said axis and opposite said tapered, radially outward, distally and laterally facing surface, and a tapered, distally and laterally facing surface perpendicular to said flat radially inward lateral surface and extending between said flat radially inward lateral surface and said tapered, radially outward distally and laterally facing surface for a predetermined longitudinal distance along the length of said tines, wherein each said tapered, radially outward, distally and laterally facing surface proximal to said tip surface is conical.

5. An all-suture anchor inserter for inserting an all-suture anchor into a bone comprising:
    an elongated shaft having an axis, a proximal end and a distal end, said distal end comprising a pair of longitudinally aligned and symmetrical, distally extending tines situated on opposite sides of said axis, each of said tines comprising a distally facing planar tip surface, a tapered, radially outward, distally and laterally facing surface proximal to said planar tip surface, a flat radially inward lateral surface situated in a plane parallel to said axis and opposite said tapered, radially outward, distally and laterally facing surface, and a tapered, distally and laterally facing surface perpendicular to said flat radially inward lateral surface and extending between said flat radially inward lateral surface and said tapered, radially outward distally and laterally facing surface for a predetermined longitudinal distance along the length of said tines, wherein each said tapered, radially outward, distally and laterally facing surface proximal to said tip surface is convex.

6. An all-suture anchor inserter for inserting an all-suture anchor into a bone comprising:
    an elongated shaft having an axis, a proximal end and a distal end, said distal end comprising a pair of longitudinally aligned and symmetrical, distally extending tines situated on opposite sides of said axis, each of said tines comprising a distally facing planar tip surface, a tapered, radially outward, distally and laterally facing surface proximal to said planar tip surface, a flat radially inward lateral surface situated in a plane parallel to said axis and opposite said tapered, radially outward, distally and laterally facing surface, and a tapered, distally and laterally facing surface perpendicular to said flat radially inward lateral surface and extending between said flat radially inward lateral surface and said tapered, radially outward distally and laterally facing surface for a predetermined longitudinal distance along the length of said tines, and further comprising a pair of opposed broaching projections situated on each tine proximally of said pair of opposed, tapered, distally and laterally facing surfaces, said opposed broaching projections extending in substantially opposite lateral directions from each of said tines.

7. An all-suture anchor and an inserter, comprising:
    an inserter having a shaft with a pair of opposing flat surfaces formed along an intermediate portion thereof, a pair of tines positioned at one end of the shaft and spaced apart to define a slot therebetween, and a pair of broaching projections extending outwardly and oppositely from each of said pair of tines;

an all suture anchor having an elongated, malleable body comprising a proximally facing proximal end and a distally facing distal end, and at least one suture filament interwoven generally lengthwise through said body that is captured in the slot between the tines so that said body rests against said opposing flat surfaces of said shaft.

8. The combination of claim 7 wherein said body has a longitudinal midpoint that is captured in said slot.

\* \* \* \* \*